(12) United States Patent
Dryer et al.

(10) Patent No.: US 8,304,455 B2
(45) Date of Patent: Nov. 6, 2012

(54) COMPOSITIONS AND METHODS OF THEIR USE FOR IMPROVING THE CONDITION AND APPEARANCE OF SKIN

(75) Inventors: Laurence Dryer, Butler, NJ (US); Dmitri Ptchelintsev, Jersey City, NJ (US)

(73) Assignee: Avon Products, Inc, New York, NY (US)

( * ) Notice: Subject to any disclaimer, the term of this patent is extended or adjusted under 35 U.S.C. 154(b) by 504 days.

(21) Appl. No.: 12/025,133

(22) Filed: Feb. 4, 2008

(65) Prior Publication Data
US 2008/0153912 A1    Jun. 26, 2008

Related U.S. Application Data

(62) Division of application No. 11/021,242, filed on Dec. 22, 2004, now Pat. No. 7,351,745.

(51) Int. Cl.
*A01N 31/00* (2006.01)
*A61K 31/10* (2006.01)
*A61K 8/02* (2006.01)

(52) U.S. Cl. ........................................ 514/712; 424/401

(58) Field of Classification Search .................. 514/712; 424/400
See application file for complete search history.

(56) References Cited

U.S. PATENT DOCUMENTS 5,472,698 A * 12/1995 Rawlings et al. ............. 424/401
6,539,946 B2 * 4/2003 Weyergans ................... 128/898

FOREIGN PATENT DOCUMENTS

| JP | 09286715 A | * | 11/1997 |
| JP | 11137212 A | * | 5/1999 |
| WO | WO 03075901 A2 | * | 9/2003 |

OTHER PUBLICATIONS

Wells, R.S. "Diseases of the Skin: Ichthyosis" The British Medical Journal, Dec 1966, vol. 2, No. 5528, pp. 1504-1506.*
Atiyeh et al. "Improving Scar Quality: A Prospective Clinical Study" Aesth. Plast. Surg., 2002, vol. 26, pp. 470-476.*

* cited by examiner

*Primary Examiner* — Sreeni Padmanabhan
*Assistant Examiner* — Kendra D Carter
(74) *Attorney, Agent, or Firm* — David M. Joyal; Joan M. McGillycuddy; Charles J Zeller

(57) ABSTRACT

The present invention relates to compositions and methods for treating, preventing and improving the condition and/or aesthetic appearance of skin, particularly, treating, preventing, ameliorating, reducing and/or eliminating fine lines and/or wrinkles of skin, where the compositions include active agents which increase expression levels of genes associated with the dermatological signs of aging. The compositions of the invention are topically applied to the skin, or are delivered by directed means to a site in need thereof, once daily in an amount effective in improving the condition and/or aesthetic appearance of skin.

7 Claims, No Drawings

US 8,304,455 B2

COMPOSITIONS AND METHODS OF THEIR USE FOR IMPROVING THE CONDITION AND APPEARANCE OF SKIN

RELATED APPLICATIONS

This is a divisional application that claims priority to, and the benefits of, co-pending U.S. patent application Ser. No. 11/021,242, filed Dec. 22, 2004.

FIELD OF THE INVENTION

This invention generally relates to cosmetic compositions and their use, and more particularly to cosmetic compositions and to their use in improving the condition and appearance of skin.

BACKGROUND OF THE INVENTION

There is an increasing demand in the cosmetics industry to develop products that may be applied topically to the skin that improve the condition and appearance of skin. Consumers are interested in mitigating or delaying the dermatological signs of chronologically or hormonally-aged or photo-aged skin, such as fine lines, wrinkles, and sagging skin, and other conditions due to a progressive degradation of the dermal-epidermal junction (DEJ) and of the cell-cell cohesion in the epidermis. During the aging process, the complexion of the skin, i.e., the color and appearance of the skin, deteriorates slowly from aging and/or exposure to sunlight. Numerous cosmetic and medical treatments have been developed in an attempt to treat aging or aged skin.

A problem commonly encountered when using an active agent or ingredient derived from a natural plant material or plant seed is the relatively low level at which they are naturally present. Such low levels frequently require relatively large amounts of natural plant material, leaf, tissue or seed to be processed in order to obtain desired or useful quantities of actives. For rare plants or plant seeds, such large amounts may be unavailable or difficult to obtain. Therefore, there remains a general need in the cosmetics industry for products that retard or counter the aging effects on the skin, and more specifically for products that produce such effects without undesirable side effects. In particular, there remains a need for topically applied cosmetic compositions that have anti-aging and skin texture benefits using non-natural materials as active components.

It would be desirable to have a topical composition comprising a synthetic active agent which improves the condition and aesthetic appearance of skin. It would also be desirable to have an effective treatment for the dermatological signs of aging.

L-theanine is a non-protein amino acid. L-theanine is considered the main component responsible for the taste of green tea. L-theanine is marketed in Japan as a nutritional supplement for mood modulation. L-theanine is a derivative of L-glutamic acid. It is a water-soluble solid substance with the molecular formula $C_7H_{14}O_3N$ and a molecular weight of 160.19. L-theanine is also known as gamma-ethylamino-L-glutamic acid, gamma-glutamylethylamide, r-glutamylethylamide, L-glutamic acid gamma-ethylamide and L-N-ethyl-glutamine.

S-Methyl-L-Cysteine is an amino acid derivative having a molecular formula of $C_4H_9NO_2S$ and molecular weight of 135.19. S-Methyl-L-Cysteine is also known as L-Cys(Me).

S-Phenyl-L-Cysteine is an amino acid derivative having a molecular formula of $C_9H_{11}NO_2S$ and molecular weight of 197.3. S-Phenyl-L-Cysteine is also known as S-phenyl cysteine.

Safe, effective and novel compositions to treat, prevent, reduce, inhibit, and/or improve the dermatological signs of aging, would be advantageous for the formulation of treatments and products for the skin. As described herein, novel and beneficial methods and compositions, as well as their mode of action, for the treatment of wrinkles and the like, as well as for personal care products for the skin, are provided by the present invention.

SUMMARY OF THE INVENTION

It is an object of the present invention to provide a topical cosmetic composition that delivers an effective level of an active component.

It is another object of the present invention to provide a topical cosmetic composition having one or more active components in a cosmetically, dermatologically, physiologically, or pharmaceutically acceptable vehicle.

It is a further object of the present invention to provide a topical composition having one or more active components, that results in increased expression of genes associated with dermatological signs of chronologically or hormonally-aged or photo-aged skin, such as fine lines, wrinkles, and sagging skin, and other conditions due to a progressive degradation of the dermal-epidermal junction (DEJ) and of the cell-cell cohesion in the epidermis, where the topical composition is a cosmetic product for the face and/or body.

It is yet another embodiment of the invention to provide a method of treating, preventing, and/or ameliorating the appearance of fine lines and/or wrinkles, comprising applying to skin a topical composition having an active agent, ingredient, or component, for example, an amino acid or modified amino acid, or combinations thereof, in an amount effective to prevent, ameliorate and/or reduce dermatological signs of chronologically or hormonally-aged or photo-aged skin, such as fine lines, wrinkles, and sagging skin, especially wrinkling due to hyperkinetic activity of facial muscle, and other conditions due to a progressive degradation of the dermal-epidermal junction (DEJ) and of the cell-cell cohesion in the epidermis.

Yet another object of the invention provides a topical cosmetic composition having an active component, which increases the expression levels of genes associated with the dermal-epidermal junction of skin, communication between the dermis and epidermis of skin, and mechanical properties of the skin, as well as, cell to cell cohesion in the epidermis of skin, anchoring of the cells of skin, communication between cells of skin, and tissue stability of skin, in order to improve the aesthetic appearance of skin.

These and other objects and advantages of the present invention, and equivalents thereof, are achieved by cosmetic compositions having a natural plant ingredient or blends thereof, and methods of use of such compositions for topical application in order to improve the aesthetic appearance of skin.

DETAILED DESCRIPTION OF THE INVENTION

The present invention relates to topical compositions having one or more active components that improve the condition or aesthetic appearance of skin and rejuvenate or enhance the skin by providing a variety of anti-aging and skin texture benefits. Improvements in the aesthetic appearance of the skin may be achieved by topical application of these cosmetic compositions to the skin on a daily basis.

One embodiment of the present invention relates to the novel use of one or more active components, where the active component is an amino acid derivative, such as but not limited to, L-theanine, L-methyl-L-cysteine, and L-phenyl-L-cysteine, in a topical cosmetic composition for application on the face and/or body in order to improve the condition and aesthetic appearance of skin, where the topical composition is preferably applied daily with the intention of leaving the composition on the affected area of skin.

In a further embodiment, the topical compositions having an active component may be used to treat, prevent, ameliorate, and/or reduce dermatological signs of chronologically aging, which represent the structural, functional, and metabolic changes in the skin that parallel the aging and degenerative changes in other body organs, or photo-aged skin, which is a separate process and largely involves damage to the collagen and elastin fibers in the skin, as fine lines, wrinkles, and sagging skin, especially wrinkling due to hyperkinetic activity of facial muscle, and other conditions due to a progressive degradation of the dermal-epidermal junction (DEJ) and of the cell-cell cohesion in the epidermis, in order to improve the condition and aesthetic appearance of skin.

Symptoms of chronological aging include: dry and thin skin, fine wrinkles, abnormal blood vessels, age spots, and benign and malignant skin tumors. Young skin renews itself more frequently than older skin. The top layers thereby lose more moisture due to the aging process, and older skin has a dryer and more dehydrated appearance. Diminished production of collagen leads to fine wrinkles initially observed around the eyes (commonly known as "crow's feet"), forehead, and other sun-exposed areas. More pronounced effects include furrows at the site of facial expression lines and sagging folds over the eyelids, neck, jaw, and arms. Within the many small, delicate blood vessels supplying nutrients to the skin, abnormalities develop. This is particularly conspicuous over the nose and cheeks. Age spots are pigmentations that surfaced as a result of deregulation of pigment cells in sun-exposed areas.

While genetics play a significant role, the number of wrinkles present is highly dependent on the amount of sun exposure. The lines in a "lived-in face," especially for those who spend a considerable amount of time outdoors, is a consequence in part of oxidative damage due to overexposure to ultraviolet (UV) sunlight—both UVA (responsible for tanning wrinkling, and melanoma) and UVB (responsible for sunburn and basal and squamous cell carcinoma). UV light may further damage skin by increasing the production of proteolytic enzymes that break down collagen, the connective tissue located beneath the dermis.

The skin is made up of multiple layers of cells that are constantly going through shedding and regeneration once every 30 days in repeated cycles. The layers may be broadly divided into two sections—the top epidermis and the underlying dermis. Histological studies of the skin show that a wrinkle is formed following a series of major cellular changes. During the early phase of aging (from age 35-45), there is a gradual and progressive slowing of cellular turnover and regeneration. This results in the skin getting thinner. As a result, the normally undulating ridge-like dermal-epidermal junction (DEJ) becomes flatter. This flatness reduces the surface area of nutritional exchange between the underlying dermis on the bottom and the epidermis on top.

Reduced nutrition to the epidermis from aging is one factor that causes cellular exhaustion and weakness. Without proper nutrition to the epidermis, cellular metabolism of the epidermal cell is slowed. Furthermore, the transportation of certain unwanted byproducts of cellular metabolism such as free radicals is reduced. The accumulation of such free radicals within the cell may lead to undesirable mutational damages in the cell and ultimately cancer.

The adhesion in the DEJ is normally supplied by Collagen 4 (a multi-sheet structure or basal layer) and collagen 7 (anchored to the sheets structure). The progressive loss of nutrients to the DEJ slows the circulation of the messengers that serve to promote the neo-synthesis process of such collagen. Without an optimal amount of collagen, the skin sags even more, propagating the dearth of nutrients. Paradoxically, matured aging skin contains more elastin, which the body uses to fill in the empty space left by the deficiency of collagen. Such elastin, unfortunately, is fragmented, calcified, and contains excessive lipids. In addition to the loss of skin thickness due to the lack of collagen support, the aging or aged skin is more loose and lacks elasticity. These two properties are hallmarks of wrinkles. This process of aging and appearance of wrinkles is accelerated during the later phase of aging (age 45 and higher). By age 50, very few women can escape wrinkles.

Embodiments of the invention relate to the discovery that an active component, such as an amino acid derivative, or combinations thereof, identified in the present invention diminish skin lines and wrinkles, as well as relieves sagging, or other conditions due to a weakened skin matrix, in a topical cosmetic, composition, or formulation. The composition is preferably applied topically to the affected area of the skin once, twice, or more daily and allowed to remain on the affected area. The daily application may be for a period of at least one week, but may be for a period of up to two, four, eight, twelve weeks or more to improve the condition and aesthetic appearance of skin.

In particular, the active agent, such as but not limited to, L-Theanine, S-Methyl-L-Cysteine, S-Phenyl-L-Cysteine, and any combination thereof, increase expression of one or more of the following genes: Beta-catenin, Collagen 4, Collagen 7, Frizzled 10, Estrogen Receptor alpha, and Hyaluronic acid synthase, such that when the composition having the active agent which is administered topically, improves the condition and aesthetic appearance of skin due to dermatological signs of aging by lessening facial lines, wrinkles, and sagging skin. The topical composition is preferably applied and left on the affected area in a daily manner.

Topical Composition

For purposes of the invention, the active agent may be derived from a natural plant material in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, or components and/or constituents found in, or isolated from, the natural plant material, and/or portions of the plant, or extracts, constituents, components, or ingredients derived either directly or synthetically from the plant, or any combinations thereof. The active agent is preferably constructed synthetically and used in the topical composition of the invention.

In a further embodiment, the active component or active agent also includes "synthetic" extracts, i.e. various combinations of natural plant material components and/or constituents that are combined to substantially mimic the composition and/or activity of the natural plant material. Such synthetic extracts are included in the term "active component." Most preferably, the synthetic extracts have substantially the same number of active components as a natural plant material. The correspondence of the numerical incidence of actives between the synthetic extracts and the natural plant material may also be described in terms of "percent commonality."

Another embodiment relates to a synthetic extract having about 50% or more commonality to the chemical composition of a natural plant material. For example, the synthetic extract has about 50% or more of the active components found in the natural plant material. The chemical composition of the synthetic extract may have about 70% or more commonality to the chemical composition of the natural plant material. A synthetic extract may have about 90% or more commonality to the chemical composition of the natural plant material.

It is to be understood that "active component" or "active agent" includes an amino acid derivative, such as but not limited to, L-Theanine, S-Methyl-L-Cysteine, S-Phenyl-L-Cysteine, and any combination thereof, synthetics of these amino acid derivatives, or a component, constituent, or extract, having similar properties or structure as these amino acid derivatives, where the component, constituent, or extract is derived from a natural plant material.

In one embodiment of the invention, the topical compositions having one or more L-Theanine, S-Methyl-L-Cysteine, S-Phenyl-L-Cysteine, and any combination thereof, are useful for improving the condition and aesthetic appearance of skin, particularly matured or maturing skin, by any one of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness, increasing skin elasticity and/or resiliency; enhancing exfoliation; improving microcirculation; decreasing and/or preventing cellulite formation; and any combinations thereof.

As stated above, the preferred active agents for use in the present invention are selected from one or more of the following amino acid derivatives: L-Theanine, S-Methyl-L-Cysteine, S-Phenyl-L-Cysteine, and any combination thereof. However, it is also contemplated that other amino acids, amino acid derivatives, or combinations thereof, may work equally as well if they increase expression levels of genes associated with dermatological signs of aging. These genes may include, but are not limited to, Beta-catenin, Collagen 4, Collagen 7, Frizzled 10, Estrogen Receptor alpha, and Hyaluronic acid synthase.

In one embodiment, the composition may have an active agent derived in an amount from about 0.0001 weight % to about 20 weight %, preferably from about 0.001 weight % to about 10 weight %, more preferably from about 0.01 weight % to about 5 weight %, and most preferably from about 0.05 weight % to about 1 weight %, based on the total weight of the composition. The active agent may be derived from a natural plant material, or synthesized, where the active agent increases expression levels of any one, or combinations thereof, of genes: Beta-catenin, Collagen 4, Collagen 7, Frizzled 10, Estrogen Receptor alpha, and Hyaluronic acid synthase. The active agents which increase expression levels of genes associated with dermatological signs of chronologically or hormonally-aged or photo-aged skin, such as fine lines, wrinkles, and sagging skin, especially wrinkling due to hyperkinetic activity of facial muscle, and other conditions due to a progressive degradation of the dermal-epidermal junction (DEJ) and of the cell-cell cohesion in the epidermis, in order to improve the condition and aesthetic appearance of skin, and the composition comprising one or more of these active agents are effective when topically applied, preferably in a daily manner. Without wishing to be bound by theory, the active agents, which increase gene expression of the aforementioned genes, exert their effects through a mechanism of action involving the dermal-epidermal junction of skin, communication between the dermis and epidermis of skin, and mechanical properties of the skin, as well as, cell to cell cohesion in the epidermis of skin, anchoring of the cells of skin, communication between cells of skin, and tissue stability of skin. Topical application of the plant also facilitates the targeted delivery of the active components without the requirement of an injection or the expertise of a health practitioner.

The active agents of the present invention are further useful in treating, preventing, arresting, ameliorating, reducing or diminishing, medical and/or cosmetic conditions of the skin. Such conditions commonly include, but are not limited to, dermatological aging (chronological aging, hormonal aging and/or actinic aging), dermatitis, skin and hair fragility, hirsutism, rosacea, dry skin, chapped skin, skin blemishes, sensitive skin, hyperpigmentation or hypopigmentation, thinning skin, roughness, keratosis, skin atrophy, wrinkles, lines, hyperplasia, fibrosis, sunburn, and any combinations thereof. The active agents of the present invention may also be useful in enhancing the general health, vitality, condition, and appearance of the skin.

Topical compositions having active agents, including but not limited to, L-theanine, S-Methyl-L-Cysteine, and S-Phenyl-L-Cysteine, which increase expression levels of genes, including, but not limited to: Beta-catenin, Collagen 4, Collagen 7, Frizzled 10, Estrogen Receptor alpha, and Hyaluronic acid synthase, improve the condition, cosmetic, and/or aesthetic appearance of skin.

Wnt proteins form a family of highly conserved secreted signaling molecules that regulate cell-to-cell interactions during embryogenesis. Wnt genes and Wnt signaling are also implicated in cancer. Insights into the mechanisms of Wnt action have emerged from several systems, including, genetics in *Drosophila* and *Caenorhabditis elegans*; as well as, biochemistry in cell culture and ectopic gene expression in *Xenopus* embryos. Many Wnt genes in the mouse have been mutated, leading to very specific developmental defects. Wnt proteins bind to receptors of the Frizzled family (FZ) on the cell surface. Through several cytoplasmic relay components, the signal is transduced to beta-catenin, which then enters the nucleus and forms a complex with transcription factor (TCF) to activate transcription of Wnt target genes.

Frizzled (Fz) genes encode a family of Wnt ligand receptors, which have a conserved cysteine-rich Wnt binding domain and include both transmembrane and secreted forms. Disturbing Wnt signaling results in aberrant hair formation, hair growth, and hair structure. Elevated expression of Fz10 was confined to developing hair follicles (Reddy, et al. "Expression of Frizzled Genes in Developing and Postnatal Hair Follicles." *Journal of Investigative Dermatology* 123 (2), 275-282, 2004; incorporated by reference).

Beta-catenin is a cytoskeletal component that enters the nucleus to act as a transcriptional cofactor. Phosphorylation of Beta-catenin induces the ubiquitination and proteolytic degradation of beta-catenin by the proteasome. Non-phosphorylated beta-catenin is stable and enters the nucleus to regulate transcription with TCF. The beta-catenin/TCF complex thereby activates genes that promote cellular survival, proliferation and differentiation during development.

Collagen, which has several forms, is a major body protein and accounts for almost 20% of the total protein in the human body. In addition to its critical role in forming support structure of the skin, it is also the main constituent of the extracellular matrix. Mutations in Collagen 7 are known to be involved in many types of epidermolysis bullosa, a human skin disease characterized by separation of dermal and epidermal layers (Pulkkinen L, et al. "Mutation analysis and molecular genetics of epidermolysis bullosa." *Matrix Biol* 18:29-42, 1999; incorporated by reference). Collagen 4 is associated with extracellular matrix and basement membrane zone formation, which is responsible for epidermal adhesion to the dermis in human skin.

Activation of ERα is responsible for many biological processes, including cell growth and differentiation, morphogenesis and programmed cell death (Katzenellenbogen, B. S. "Estrogen receptors: bioactivities and interactions with cell signaling pathways" *Biol. Reprod*, 54, 287-293, 1996; Katzenellenbogen, B. S., et al. "Antiestrogens: mechanisms of action and resistance in breast cancer" *Breast Cancer Res. Treat.*, 44, 23-38, 1997; both incorporated by reference). In addition, ERα plays an important role in the development and progression of breast cancer by regulating genes and signaling pathways involved in cellular proliferation.

Hyaluronic acid (HA) is a polysaccharide found in the extracellular mactrix of vertebrate tissues and in the surface coating of certain Streptococcus and Pasteurella bacterial pathogens. HA synthases (HASs) are the enzymes that polymerize HA. HA is known to be secreted out of the cell; and accordingly, HASs are normally found in the outer membranes of the organisms.

Increases in expression levels of specific genes associated with the progressive degradation of the dermal-epidermal junction (DEJ), including with poor communication between the dermis and epidermis, poor mechanical properties of the skin; and of the cell-cell cohesion, including poor anchoring of the cells, poor cell-cell communication and poor tissue stability, in the epidermis are particularly useful in the topical compositions of the present invention. In one embodiment, the useful genes include, but are not limited to, Beta-catenin, Collagen 4, Collagen 7, Frizzled 10, Estrogen Receptor alpha, and Hyaluronic Acid Synthase. Any natural plant material, including an extract derived therefrom, that increases expression of any one of these genes, is found useful in the topical compositions of the present invention.

Gene expression may be measured by the determination of RNA levels in cultured cells, for example, using techniques such as Northern blot technology and the polymerase chain reaction (PCR), e.g., "real time" PCR and reverse transcription PCR (RT PCR) as practiced in the art. (see, e.g., J. Sambrook et al., 1989, *Molecular Cloning: A Laboratory Manual*, Cold Spring Harbor Laboratory, Cold Spring Harbor, N.Y.; R. Higuchi et al., 1992, *Biotechnology*, 10:413-417; R. Higuchi et al., 1993, *Biotechnology*, 11:1026-1030; E. S. Kawasaki, 1990, "Amplification of RNA", In: *RNA Protocols: A Glide to Methods & Applications*, M. A. Innis et al., Academic Press, San Diego, Calif., pp. 21-27; all of which are herein incorporated by reference). In addition, gene expression in skin, skin substitute, or cultured cells may be evaluated using gene (cDNA) arrays (microarrays or nucleic acid genechip test arrays comprising membrane, glass, or plastic support materials), serial analysis of gene expression (SAGE), (e.g., as described by V. E. Velculescu et al., *Science*, 270(5235):484-487, 1995; A. Lal et al., *Cancer Res.*, 59(21): 5403-5407, 1999; both of which are herein incorporated by reference), or differential display techniques. Example 3 shows the results of gene expression of Beta-catenin, Collagen 4, Collagen 7, Frizzled 10, Estrogen Receptor alpha, and Hyaluronic Acid Synthase upon treatment with natural plant materials.

The invention encompasses using genes associated with dermatological signs of aging, such as fine lines, wrinkles, and sagging skin as a biomarker for compounds which may improve the condition and appearance of skin. If expression levels of such nucleic acid biomarkers are elevated in the presence of a natural plant material, the natural plant material may be used in a topical composition of the invention for improving the condition and appearance of skin. Such assays embrace a variety of methods for measuring nucleic acid levels in cells that have been exposed to one or more test substances. Suitable methods include detection and evaluation of gene activation or expression of, for example, DNA, RNA, or mRNA. As non-limiting examples, polymerase chain reaction (PCR) assays (e.g. RT-PCR), Northern blotting, in situ hybridization, and other assays as known and practiced in the art may be employed to quantify RNA in cells being assayed for tolerance to a particular treatment (see, e.g., J. O'Connell, 2002, *RT-PCR Protocols*, Humana Press, Totowa, N.J.; R. Rapley and D. L. Manning, 1998, *RNA Isolation and Characterization Protocols*, Humana Press; R. Rapley, 2000, *Nucleic Acid Protocols Handbook*, Humana Press; all of which are herein incorporated by reference). In accordance with such assays, if levels of at least one nucleic acid biomarker are elevated in the presence of one or more test substances, this may predict that the substance(s) will improve the dermatological signs of aging. These substances, or natural plant materials, may then be used in a topical composition, preferably applied daily to the skin, in order to treat, prevent, ameliorate, and/or reduce, signs of dermatological aging, especially fine lines, wrinkles, and sagging skin, thereby improving the condition and aesthetic appearance of skin.

In one embodiment, the topical compositions have an amino acid derivative active agent, such as but not limited to, L-Theanine, S-Methyl-L-Cysteine, and S-Phenyl-L-Cysteine, or any amino acid derivative that increases expression levels of one or more genes of, but not limited to, Beta-catenin, Collagen 4, Collagen 7, Frizzled 10, Estrogen Receptor alpha, and Hyaluronic acid synthase, in an amount of amino acid derivative active agent ranging from about 0.0001 weight % to about 20 weight %, preferably from about 0.001 weight % to about 10 weight %, more preferably from about 0.01 weight % to about 5 weight %, and most preferably from about 0.05% to about 1%, based on the total weight of the composition. These topical compositions are useful in improving the condition and aesthetic appearance of skin.

Formulations

In accordance with the invention, compositions comprising amino acid derivative active agents include, but are not limited to, topically applied formulations, anti-oxidants, anti-inflammatories, sunscreens, cosmetics, including makeup, formulations for reducing dermatological signs of aging, including wrinkles, fine lines, and sagging skin, topicals, skin penetration enhancers, and the like. Also in accordance with this invention, the active agents, or amino acid derivatives synthesized or derived from natural plant materials or components thereof, and additional constituents comprising such compositions may be formulated in a variety of product forms. The compositions may be prepared in targeted delivery systems, e.g. creams, lotions, masks, gels, toners, serums, transdermal patches, and the like, particularly for topical administration. Targeted delivery and/or penetration enhancement may also be achieved by iontophoresis.

The present invention further provides the compositions comprising the amino acid derivative active agents preferably for topical administration or for targeted delivery without inducing significant irritation. The inventive compositions are suitable for all skin types, such as sensitive, normal, dry, or oily, preferably sensitive to dry skin. In particular embodiments, the compositions may be preferably for dry skin. The compositions are applied to the skin for a period of time sufficient to improve the condition or aesthetic appearance of skin. The topical compositions may be applied topically once, twice, or more daily. The daily application may be applied for a period of one week, two weeks, four weeks, or more. The preferred topical composition or formulation may be applied and left on the affected area once daily.

The topical compositions may be formulated into liposomes which may comprise other additives or substances, and/or which may be modified to more specifically reach or remain at a site following administration. These formulations enable the active agents to more improve the condition and aesthetic appearance of skin.

Another embodiment of the invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition," incorporated herewith) and the like, as well as other botanicals such as aloe, chamomile, and the like, and as further described below.

Also, embraced by the invention are transdermal modes of delivery, such as patches and the like, with or without a suitable penetration enhancers. The methods and compositions embodied by the invention provide a means by which the active agents or components may be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846; 5,223,262; 4,820,724; 4,379,454; and 4,956,171, all of which are incorporated herein by reference and such descriptions are not meant to be limiting, The transdermal mode of storing and delivering the compositions onto the skin, including hair, and forming the active composition is convenient and well-suited for the purposes of an embodiment of the present invention. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

The amino acid derivative active agents of the present invention are preferably contained in a cosmetically, dematologically, physiologically, and pharmaceutically acceptable vehicle, medium, diluent or carrier, for use in treating, reducing, ameliorating, or preventing conditions associated with excess accumulation, production, or excretion of sebum and excess accumulation or production of subcutaneous fat.

In an embodiment embracing topical application, the compositions of this invention comprise a medium (vehicle, diluent or carrier) that is compatible with human skin, including hair. The compositions can be formulated as an aqueous phase, an oil phase, alcohol, or aqueous/alcohol-based solutions, ointments, lotions, gels, a wax-in-water emulsion, or water-in-oil, oil-in-water, of water-oil-water triple emulsions having the appearance of a cream or gel, microemulsions, or aerosols.

The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In one embodiment, the composition may include an aqueous phase which may contain water or a mixture of water and at least one hydrophilic organic solvent in particular an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 weight % to about 99.99 weight %, based upon the total weight of the composition.

Yet another embodiment when the composition of the invention is in the form of an emulsion, the composition may also optionally comprise a surfactant, preferably in an amount of from about 0.1 weight % to about 30 weight %, and in particular, from about 1 weight % to about 20 weight %, based upon the total weight of the composition.

In a further embodiment of the invention, the composition may also comprise a thickening polymer such as a polyurethane, a polyacrylic homopolymer or copolymer, a polyester, or a hydrocarbon-based resin.

One embodiment of the invention further relates to a composition of the invention which may also comprise an oil phase containing oil soluble or oil dispersible ingredients that are liquid at room temperature (25° C.) and/or oily or waxy substances that are solid at room temperature, such as waxes, semi-solids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, preferably from about 1 weight % to about 80 weight % by weight of the oil phase.

The oil phase of the composition of the invention may also comprise one or more cosmetically acceptable organic solvents. These solvents are present in an amount of about 0 weight % to about 60 weight %, preferably about 1 weight % to about 30 weight %, based on the total weight of the composition, and may be selected from the group consisting of lipophilic organic solvents, amphiphilic organic solvents and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetics field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition. The nature of these ingredients and their amounts must be compatible with the production of the compositions of the invention.

The composition of the invention may also comprise an additional particulate phase, typically present in an amount of about 0 weight % to about 30 weight %, based upon the total weight of the composition, preferably from about 0.05 weight % to about 20 weight %, and which can comprise pigments and/or pearlescent agents and/or fillers used in cosmetic compositions. Suitable inorganic pigments include, but are not limited to, titanium oxide, zirconium oxide and cerium oxide, as well as zinc oxide, iron oxide, chromium oxide and ferric blue. Suitable organic pigments include, but barium, strontium, calcium, and aluminium lakes and carbon black. Suitable pearlescent agents include mica coated with titanium oxide, with iron oxide, or with natural pigment.

Fillers are normally present in an amount of about 0 weight % to about 30 weight %, based on the total weight of the composition, preferably about 0.5 weight % to about 15 weight %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Corning), and silicone resin microbeads (Tospearl from Toshiba).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present invention may contain from about 0 weight % to about 20 weight % waxes, based upon the total weight of the composition.

The gums are generally high molecular weight PDMSs, cellulose gums or polysaccharides, and the semi-solid materials are generally hydrocarbon-based compounds, such as, but not limited to, lanolins and derivatives thereof, or alternatively PDMSs. The compositions of the present invention may contain from about 0 weight % to about 25 weight % gums, based upon the total weight of the composition, typically from about 0.1 weight % to about 10 weight %.

More particularly, the compositions for topical application can be in the form of a protective care composition for the skin, preferably for the face, the neck, the hands, the feet, or other areas of the body. Non-limiting examples include day creams or lotions, night creams or lotions, salves, sunscreen creams, fluid lotions, oils, ointments, gels, masks, body milks, makeup (a foundation), artificial tanning compositions, depilatories, emulsifiers, patches, or a solid which is poured or cast as a stick or a dish, for example.

Another particular embodiment of the present invention is directed to the delivery of the described compositions comprising one or more active agents by targeted delivery systems, for example, liposomes, microspheres (see, e.g., U.S. Pat. No. 5,770,222 to Unger et al., incorporated herein by reference), and the like, so that the compositions containing active constituents may more readily reach and affect the dermal-epidermal junction layer of the area where the composition is topically applied, e.g., face or neck, or other affected areas of the skin.

In another embodiment, the topical compositions of the present invention may also include one or more of the following: a skin penetration enhancer, an emollient, a skin plumper, an optical diffuser, a sunscreen, an exfoliation promoter, and an antioxidant. Details with respect to these and other suitable cosmetic ingredients can be found in the *International Cosmetic Ingredient Dictionary and Handbook* (ICID), 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 weight % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 weight % to about 20 weight % of the total weight of the composition.

A sunscreen protects the skin from damaging ultraviolet rays. In an illustrative embodiment of the invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 weight % to about 30 weight % of the total weight of the composition. The addition of a sunscreen may protect the skin from ultraviolet radiation.

The compositions of the invention having sunscreen bring about additional improvements to the aesthetic appearance of skin, including at least one of the following: minimizes sunburning, minimizes tanning, and reduces redness.

In an embodiment of the invention, compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. (See also, ICID at p. 2205).

When an embodiment of the invention includes an exfoliation promoter, the composition has about 0.1 weight % to 30 weight %, preferably about 1 weight % to about 15 weight % and more preferably about 1 weight % to about 10 weight %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy-functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 weight % to about 10 weight %, and more preferably from about 0.01 weight % to about 5 weight % based on the total weight of the composition. See also, ICID at p. 2184.

In an embodiment of the invention, the composition may also have one or more of the following cosmetic and pharmaceutical active agents, excipients, ingredients, or adjuvants: anesthetics, antibiotics, e.g., erythromycins and tetracyclines, salicylic acids, anti-allergenics, antifungals, antiseptics, anti-irritants, anti-inflammatory agents, antimicrobials, analgesics, nitric oxide synthase inhibitors, insect repellents, self-tanning agents, skin penetration enhancers, skin cooling agents, chelating agents, colorants including dyes, lakes and pigments that may be untreated or chemically surface treated to improve wetability or some other property, demulcents, emollients, emulsifiers, fragrances, humectants, lubricants, skin protectants, moisturizers, pH adjusters, preservatives, stabilizers, surfactants, thickeners, film formers, plasticizers, viscosity modifiers, vitamins, or any mixtures thereof. The amounts of these various substances are those that are conventionally used in the cosmetic or pharmaceutical fields to achieve their intended purposes, for example, they may constitute from about 0.01 weight % to 20 weight % of the total weight of the composition.

Non-limiting examples of active agents for formulating into the compositions of the invention include those reagents having an effect on the treatment of wrinkles and/or fine lines, in addition to the Alisma orientale actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These actives may be formulated, for example, in amounts of from about 0.0001 weight % to 5 weight % based on the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Emulsifiers are typically present in the compositions of the invention in an amount of about 0.01 weight % to 30 weight %, and preferably from about 0.1 weight % to 30 weight % based on the total weight of the composition. However, not all compositions will necessarily include emulsifiers. (See e.g., ICID at p. 2276-2285).

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate. (See, e.g., ICID at p. 2293-2299).

The topical compositions of the present invention may include, and their utility can be enhanced by one or more humectants, such as ureas, pyrrolidone carboxylic acids, amino acids, sodium hyaluronates, certain polyols and other compounds with hygroscopic properties. (See, ICID at p. 2244).

The general activity and mildness to skin of the present topical compositions can also be enhanced by neutralization to pH about 3.5 to about 7.0, most preferably from pH about 3.7 to about 5.6. This neutralization is preferably accomplished with one or more of ammonium hydroxide, potassium hydroxide, sodium hydroxide, arginine or other amino acids, and/or tri ethanol amine.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The amino acid derivative active agents of the present invention are preferably contained in a cosmetically, dermatologically, physiologically, or pharmaceutically acceptable vehicle, medium, diluent or carrier. The topical composition comprising the amino acid derivative active agents may be further formulated according to procedures known in the art to provide cosmetic compositions such as emulsions, gels, creams, lotions, masks, toners, serums, oils, water-in-oil, oil-in-water, water-oil-water triple emulsions having the appearance of a cream or gel, microemulsions, ointments, pastes, sticks, cakes, pencils, aerosol, and essences, as well as other topical cosmetic vehicles. It is also contemplated that topical compositions of the present invention can be incorporated into delivery systems such as liposomes and topical patches, tapes, and sprays. In addition, the compositions can be in the form of vesicular dispersions containing ionic and/or non-ionic lipids, as described above. Dosage units suitable for such compositions are formulated according to the conventional knowledge and techniques used in the art.

In a further embodiment of the invention, the compositions for topical application may be in the form of a protective care composition for the skin, preferably for the face, the neck, the hands, the feet, or other areas of the body. Non-limiting examples include day creams or lotions, night creams or lotions, sunscreen creams, lotions, or oils, body milks, makeup (a foundation), artificial tanning compositions, depilatories, and patches.

Methods of Using Topical Compositions

In another embodiment, the present invention encompasses a method of improving the condition and aesthetic appearance of skin, comprising applying to an affected area of skin, a composition containing an active agent, including but not limited to: L-Theanine, S-Methyl-L-Cysteine, and S-Phenyl-L-Cysteine, or combinations thereof, or any active agent that increases expression levels of any one, or combinations thereof, of genes: Beta-catenin, Collagen 4, Collagen 7, Frizzled 10, Estrogen Receptor alpha, and Hyaluronic acid synthase.

One embodiment of the invention relates to methods of applying an effective amount of an active agent, preferably an amino acid derivative, to induce expression of at least one gene associated with the epidermal-dermal junction, communication between the dermis and epidermis, mechanical properties of the skin, cell-cell cohesion in the epidermis, anchoring of the cells, cell-cell communication, and tissue stability, to an affected area of the skin. The topical composition is preferably applied once daily and remains on the affected area of the skin, where the affected area of the skin includes, but is not limited to the face, neck, legs and thighs, and overall body.

Another embodiment of the present invention relates to a method of improving the condition and aesthetic appearance of skin and comprises applying to the skin, or introducing via a directed mode of delivery, a composition including one or more active agents in an amount effective to improve the aesthetic appearance of conditions related to skin, where the active agent increases expression of one or more of the following genes: Beta-catenin, Collagen 4, Collagen 7, Frizzled 10, Estrogen Receptor alpha, and Hyaluronic acid synthase.

In a specific embodiment, the component is an active agent, as previously described, in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

As will be appreciated by the practitioner, cosmetic treatments comprising compositions containing natural plant materials, including extracts, components, and/or constituents of the invention, such as the active agents (L-Theanine, S-Methyl-L-Cysteine, S-Phenyl-L-Cysteine, and any combination thereof) may be carried out, for example, by topically applying the cosmetic composition as described herein according to the routine technique for administering such compositions. The topical cosmetic composition preferably is applied once daily for a period of at least one week, but may include a period of about 2, 4, 8, or 12 weeks. The cosmetic composition is preferably applied to the face and neck, but may be applied to any area of skin in need of aesthetic improvement, where the cosmetic composition remains on the affected area of skin, and preferably not removed or rinsed off the skin. Routine and commonly practiced techniques encompass the application of creams, lotions, gels, masks, sera, ointments, patches, makeup, makeup-removing milks, sunscreen compositions, or the like, to the skin. Preferably the cosmetic composition is a topical leave on formulation, where spraying as a form of application is also envisioned.

EXAMPLES

The following examples describe specific aspects of the invention to illustrate the invention and provide a description of the present methods for those skilled in the art. The examples should not be construed as limiting the invention, as the examples merely provide specific methodology useful in the understanding and practice of the invention and its various aspects.

Example 1

Cell Culturing

A vial of cryopreserved normal human epidermal keratinocytes (Adult or Neonatal) was removed from liquid N2 and placed in a 37° C. water bath for 1-2 minutes, or until completely thawed. The vial was then removed from the water bath and the excess water was wiped off. The vial was placed into a cell culture hood for sterility. The vial was wiped with 70% ethanol to air dry for 30 seconds. While in the cell culture hood, the cells were removed from the vial and placed into a 50 ml tube. The appropriate growth media (5 ml) was added drop wise while agitating the tube, allowing uniform mixture of the cells and medium while limiting cell death due to osmotic changes caused by freezing media, Medium (25 ml) was added to the 50 ml tube to bring the volume up to 30 ml. Into two 75 cm2 flasks, medium/cell solution (15 ml) was added, or to six 25 cm2 flasks, medium (5 ml) was added. Flasks were recapped and placed horizontally in a 37° C. humidified incubator with 5% CO2 for 24 hours. After 24 hours, the old medium was aspirated and fresh room temperature growth medium (15 ml) was added onto the cells. Prior to adding the fresh growth medium, it was brought up to room temperature using a room temperature water bath without the cover. The flasks containing cells with fresh media were placed back into the 37° C. incubator. Flasks containing the old media was replaced with fresh media repeatedly until the desired confluence (75%) was reached.

Plating and Treatment

When the cells reached the desired confluency, they were removed from the incubator and the media was aspirated off using a vacuum trap. Hank's Buffered Saline Solution (HBSS; 10 ml of 1X; Mediatech, Inc.; Herndon, Va.) was placed into the flask and the entire surface area rinsed. The HBSS was then aspirated. Trypsin (1X; Mediatech, Inc.) was added in a 5 ml volume. The flasks were placed back into the incubator for 8 minutes. The flasks were taken from the incubator and 15 ml of Trypsin Neutralizing Solution (1X; Cascade Biologics; Portland, Oreg.) was added to each flask to neutralize the trypsin. The medium/cell solution was removed from the flasks and placed into a 50 ml polypropylene tube. The cells were spun down using a bench top centrifuge at 1100 rpm for 6 minutes at room temperature. After spinning the cells, they were resuspended in growth medium (Basal Medium: Epilife medium with calcium chloride (Cascade Biologics, Inc.); supplemented with 1% human keratinocyte growth factor (Cascade Biologics); 1% Penicillin/Streptomycin (Mediatech, Inc.). The cells were resuspended by pipetting up and down. Cell culture was then placed into 100 mm tissue culture-treated plates in 10 ml volumes for incubation in a 37° C. humidified incubator with 5% CO2 until 75% confluency is reached. When confluency was reached, medium was removed and replaced with fresh growth medium containing the test active at a specific concentration. Each test active was diluted in growth medium from a 10% stock vial containing a vehicle (i.e., water, ethanol, DMSO) and the test active. Each vehicle was tested along side the test active as a control. The 100 mm tissue culture-treated plates were placed back into the 37° C. humidified incubator with 5% CO2 for varying amount of times in order to establish a time course for actives being tested. The tissue culture plates were collected at 1 hour, 4 hour, 8 hour, 24 hours, and 32 hours. At each time point, the growth medium was aspirated and the cells were washed with 1X Phosphate-buffered saline (PBS). The 1X PBS was removed and the 100 mm tissue culture plates were wrapped in parafilm and stored in −80° C. until needed.

RNA Isolation

Parafilm was removed from the outside of the 100 mm tissue culture plates and 2 ml of Trizol Reagent (1X; Invitrogen, Corp.; Carlsbad, Calif.) was added to the cells. The plate was scraped and the solution was placed into 2-1.7 ml microcentrifuge tubes. Chloroform (250 ml) was added to each tube and vortexed for 15-30 seconds. Each tube was incubated at room temperature (25° C.) for 3-5 minutes and centrifuged at 12,000 rpm at 4° C. for 10 minutes. The top layer of the solution was removed without disturbing the two bottom layers and placed into a separate 1.7 ml microcentrifuge tube. Ice cold isopropanol (1.0 ml) was added to the tube and incubated on ice for 10-15 minutes. The sample was centrifuged for 15 minutes at 4° C. and at 12,000 rpm. Isopropanol was poured off and ice cold 70% ethanol (1 ml) was added to the tube in order to remove the salt precipitate on the RNA sample. The sample was centrifuged for 10 minutes at 4° C. and at 12,000 rpm. The 70% ethanol was poured off and ice cold 100% ethanol was added. The sample was centrifuged for 10 minutes at 4° C. and at 12,000 rpm. The tube was dried by inverting and removing all of the 100% ethanol from the tube. The tube was stored in −80° C., either diluted in RNase-free water or dried.

Example 2

PCR Gene Expression Using Active Agents

Gene expression levels of six different genes associated with dermatological signs of aging, specifically, Beta-catenin, Collagen 4, Collagen 7, Frizzled 10, Estrogen Receptor alpha, and Hyaluronic Acid Synthase, were shown to increase in the presence of one or more of the following amino acid derivatives: L-Theanine, S-Methyl-L-Cysteine, and S-Phenyl-L-Cysteine. The polymerase chain reaction (PCR) assay was performed as is commonly practiced in the art (See, e.g., J. Sambrook et al., 1989, *Molecular Cloning: A Laboratory Manual*, Cold Spring Harbor Laboratory, Cold Spring Harbor, N.Y.). Specific thermocycle parameters used were as follows: 1 cycle, 1 minute, at 95° C.; 40 cycles, 12 seconds, at 95° C.; and 1 cycle, 30 seconds, at 60° C. in a volume of 50 microliters.

TABLE 1

|  | Beta-Catenin | | Collagen 4 | | Collagen 7 | |
| --- | --- | --- | --- | --- | --- | --- |
|  | Transcript # | p | Transcript # | p | Transcript # | p |
| L-Theanine | 10.30503162 | 0.004 | 10.79423 | 0.001 | 12.86896 | 0.003 |
|  | 8.677921366 |  | 9.560602 |  | 10.72413 |  |
|  | 8.677921366 |  | 10.48582 |  | 11.43908 |  |
| S-Methyl-L-Cysteine | 10.38824789 | 0.003 | 10.82958 | 0.002 | 16.54643 | 0.001 |
|  | 9.955404229 |  | 9.352818 |  | 16.54643 |  |
|  | 8.656873243 |  | 9.845072 |  | 14.83473 |  |
| S-Phenyl-L-Cysteine | 14.67280624 | 0.009 | 7.416321 | 0.003 | 35.45928 | 0.002 |
|  | 15.48796214 |  | 8.343361 |  | 34.38475 |  |
|  | 11.41218263 |  | 8.806881 |  | 30.08666 |  |

Only statistically significant numbers shown. Transcript numbers are normalized to vehicle control. Indicated p value from t test with vehicle control.
(—): Not statistically significant
$p < 0.05$: Statistically significant

TABLE 2

|  | Frizzled 10 | | Estrogen Receptor alpha | | Hyaluronic acid synthase | |
| --- | --- | --- | --- | --- | --- | --- |
|  | Transcript # | p | Transcript # | p | Transcript # | p |
| L-Theanine | 17.67894 | $4.42 \times 10^{-4}$ | 13.02993 | 0.034 | 10.53329 | 0.09 |
|  | 16.48037 |  | 12.39432 |  | 7.971142 |  |
|  | 17.07965 |  | 7.627276 |  | 8.113484 |  |

TABLE 2-continued

|  | Frizzled 10 | | Estrogen Receptor alpha | | Hyaluronic acid synthase | |
| --- | --- | --- | --- | --- | --- | --- |
|  | Transcript # | p | Transcript # | p | Transcript # | p |
| S-Methyl-L-Cysteine | 18.65237<br>16.26104<br>18.41324 | 0.002 | 6.087021<br>5.072518 | 0.03 | — | — |
| S-Phenyl-L-Cysteine | 34.67686<br>26.66989<br>30.62372 | 0.008 | 8.119927<br>10.98578<br>8.59757 | 0.01 | 3.636858<br>3.636858<br>3.42295 | $4.8 \times 10^{-4}$ |

Only statistically significant numbers shown. Transcript numbers are normalized to vehicle control. Indicated p value from t test with vehicle control.
(—): Not statistically significant
p < 0.05: Statistically significant The content of all patents, patent applications, published articles, abstracts, books, reference manuals and abstracts, as cited herein are hereby incorporated by reference in their entireties to more fully describe the state of the art to which the invention pertains.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A topical anti-dermatological aging composition comprising:
 (a) an active agent in an amount from about 0.0001 weight % to about 20 weight %, based upon the total weight of the composition, wherein the active agent is selected from the group consisting of: S-Phenyl-L-Cysteine: L-Theanine and S-Phenyl-L-Cysteine; S-Phenyl-L-Cysteine and S-Methyl-L-Cysteine; and L-Theanine and S-Phenyl-L-Cysteine and S-Methyl-L-Cysteine; and
 (b) a cosmetically, dermatologically, pharmaceutically, or physiologically acceptable vehicle.

2. The composition of claim 1, wherein said active agent increases expression levels of at least one gene selected from the group consisting of: Beta-catenin, Collagen 4, Collagen 7, Frizzled 10, Estrogen Receptor alpha, Hyaluronic acid synthase, and combinations thereof.

3. The composition of claim 2, wherein the active agent is present in an amount effective to improve the condition and/or aesthetic appearance of skin.

4. The composition of claim 3, wherein said composition is applied for a period of time sufficient to improve the condition and/or aesthetic appearance of skin.

5. The composition of claim 4, wherein said applying of the composition occurs at least once daily for a period of time sufficient to improve the condition and/or aesthetic appearance of skin.

6. The composition of claim 5, wherein the active agent is present in an amount from about 0.001 weight % to about 10 weight %, based upon the total weight of the composition.

7. The composition of claim 6, wherein the improvement in aesthetic appearance is selected from the group consisting of: reducing dermatological signs of chronological aging, photo-aging, hormonal aging, and/or actinic aging; reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; reversing of loss of glycosaminoglycans and/or collagen; ameliorating the effects of estrogen imbalance; skin atrophy; reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

* * * * *